(12) United States Patent
Lawrenson et al.

(10) Patent No.: US 11,238,748 B2
(45) Date of Patent: Feb. 1, 2022

(54) CUSTOMIZATION OF HELP INFORMATION BASED ON EEG DATA

(71) Applicant: Telefonaktiebolaget LM Ericsson (publ), Stockholm (SE)

(72) Inventors: Matthew John Lawrenson, Chesterfield, MO (US); Julian Charles Nolan, Pully (CH)

(73) Assignee: TELEFONAKTIEBOLAGET LM ERICSSON (PUBL), Stockholm (SE)

( * ) Notice: Subject to any disclaimer, the term of this patent is extended or adjusted under 35 U.S.C. 154(b) by 0 days.

(21) Appl. No.: 17/021,462

(22) Filed: Sep. 15, 2020

(65) Prior Publication Data
US 2020/0410883 A1    Dec. 31, 2020

Related U.S. Application Data

(63) Continuation of application No. 15/521,143, filed as application No. PCT/SE2014/051252 on Oct. 24, 2014, now Pat. No. 10,810,896.

(51) Int. Cl.
| | |
|---|---|
| G09B 5/06 | (2006.01) |
| G06F 9/451 | (2018.01) |
| G09B 5/04 | (2006.01) |
| G09B 19/00 | (2006.01) |
| A61B 5/16 | (2006.01) |
| A61B 5/00 | (2006.01) |

(Continued)

(52) U.S. Cl.
CPC .............. *G09B 5/065* (2013.01); *A61B 5/163* (2017.08); *A61B 5/165* (2013.01); *A61B 5/369* (2021.01); *A61B 5/7475* (2013.01); *G06F 9/453* (2018.02); *G09B 5/02* (2013.01); *G09B 5/04* (2013.01); *G09B 19/0053* (2013.01); *A61B 5/1103* (2013.01)

(58) Field of Classification Search
CPC ...................................................... G09B 5/065
USPC ......................................................... 434/236
See application file for complete search history.

(56) References Cited

U.S. PATENT DOCUMENTS

| | | |
|---|---|---|
| 7,865,837 B1 | 1/2011 | Huff |
| 2006/0257834 A1 | 11/2006 | Lee et al. |

(Continued)

OTHER PUBLICATIONS

Farwell, L.A., "Talking off the top of your head: toward a mental prosthesis utilizing event-related brain potentials," Electroencephalography and clinical Neurophysiology. 1988. 70: 510-523.

(Continued)

*Primary Examiner* — Kesha Frisby
(74) *Attorney, Agent, or Firm* — Rothwell, Figg, Ernst & Manbeck, P.C.

(57) ABSTRACT

A method is implemented by a computing device for helping a particular user use a user interface (UI). Electroencephalography (EEG) data is obtained that indicates brain activity of a particular user during a period in which that user views the UI and/or interprets help information that describes how to use the UI. Based on the EEG data, the computing device selects, from among multiple predefined cognitive states, the one or more cognitive states that characterize the particular user during the period. The computing device assists the particular user to use the UI by customizing the help information for the particular user based on the one or more selected cognitive states. A complementary computing device and computer program product are also disclosed.

21 Claims, 5 Drawing Sheets

(51) Int. Cl.
*A61B 5/369* (2021.01)
*G09B 5/02* (2006.01)
*A61B 5/11* (2006.01)

(56) References Cited

U.S. PATENT DOCUMENTS

2011/0091847 A1 4/2011 Carroll et al.
2011/0159467 A1 6/2011 Peot et al.
2014/0178843 A1 6/2014 Smyth

OTHER PUBLICATIONS

International Search Report and Written Opinion issued in International application No. PCT/SE2014/051252, dated Jul. 2, 2015, 10 pages.
"Brain-computer interface," Wikipedia, dated Oct. 24, 2014, 34 pages.

CUSTOMIZATION OF HELP INFORMATION BASED ON EEG DATA

CROSS-REFERENCE TO RELATED APPLICATIONS

This application is a continuation of U.S. application Ser. No. 15/521,143, filed on Apr. 21, 2017 (status pending), which is the National Stage Entry of International Patent Application No. PCT/SE2014/051252, filed on Oct. 24, 2014. The above identified applications are incorporated by this reference.

TECHNICAL FIELD

This application relates to customizing help information, and more particularly to customizing help information based on electroencephalography (EEG) data.

BACKGROUND

Electroencephalography (EEG) is the measurement of electrical activity in a person's brain as measured on a person's scalp. The electrical activity is derived from ionic current flow within the brain's neurons, and can therefore serve as an indication of activity within the brain. By localizing measurements on a subject's scalp, the EEG data can be identified in various brain locations supporting mental processing. Because different areas of the brain are associated with different types of processing, EEG can provide an indication as to the cognitive state and cognitive activity of the person being monitored.

Figure 1:
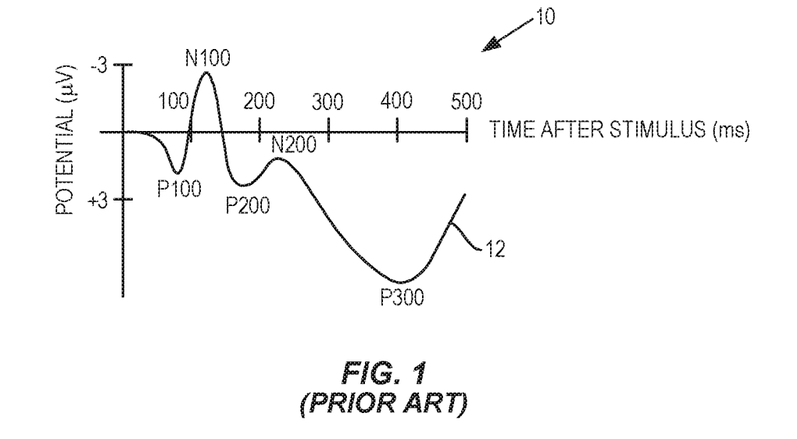
FIGS. 1-2 illustrate some examples of known ERPs.
Figure 2:
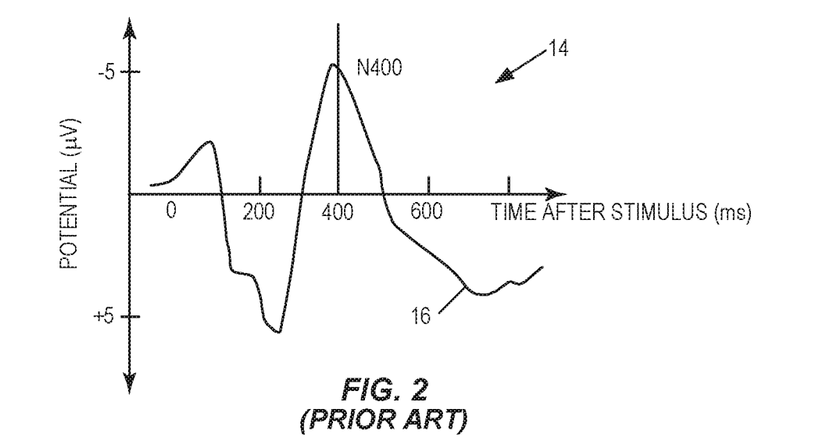

Event-related potentials (ERPs) can be determined from EEG data to measure responses to specific events. A variety of ERPs are known to those of ordinary skill in the art. These include P300, N200, P200, etc. The "P" or "N" preceding an ERP name refers to whether it is a positive or negative measured potential, and the numeric value (e.g., 200, 300) typically refers to how long after a stimulus the measurement occurred. An example stimulus could include a user viewing a specific image or hearing a sound, for example. FIGS. 1 and 2 include graphs 10, 14 that illustrate example brain potentials 12, 16 and example ERPs of those measured potentials.

The P300 ERP, for example, is a positive EEG signal occurring approximately 300 ms after a given stimulus. The P300 ERP is related to the categorization of an event, and is stronger when an event is recognized. It can therefore be used to determine whether or not a stimulus is known to a user. It can be divided into "P3a" and "P3b", where P3a relates to more rare instances (i.e., where more effort is required to recollect the stimulus), and P3b relates to stimuli that are easier to recollect.

The N200 ERP is a negative EEG signal occurring approximately 200 ms after a given stimulus, and can be associated with stimulus identification, attention, and inhibition of motor responses.

The P200 ERP (also referred to as "P2") is a positive EEG signal occurring approximately 200 ms after a given stimulus. It is related, among other things, to the processing of language. It can be used to detect, for example, if a word that is not expected by a user appears in a phrase.

Figure 3:
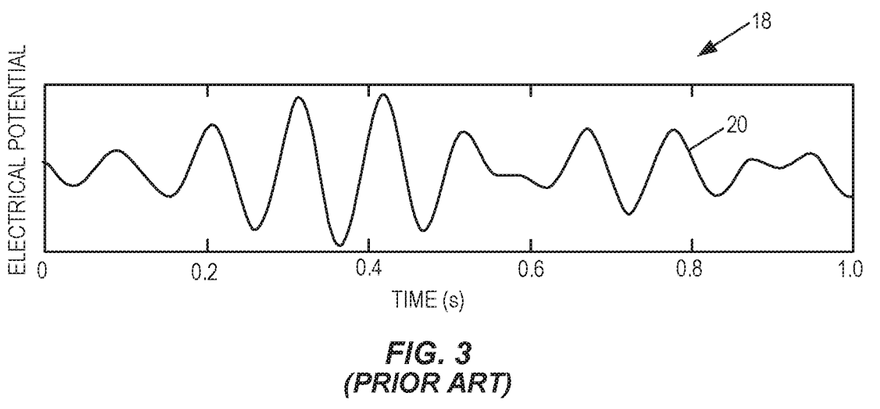
FIG. 3 illustrates example neural oscillations of an alpha wave.

EEG data may also include measurements of neural oscillations. Based on the frequency of neural oscillations, a type of brain wave can be detected. For example, theta waves have a frequency range of 4-7 Hz, alpha waves have a frequency range of 7.5-12.5 Hz, and beta waves have a frequency range of 12.5-30 Hz. Neural oscillations have been linked to cognitive states, such as awareness and consciousness. FIG. 3 is a graph 18 showing example neural oscillations 20 for an alpha wave.

EEG data can be measured using a so-called "brain computer interface" (BCI) which measures brain activity and communicates those measurements to a computing device. BCIs have historically required a user to wear a cap containing many EEG sensors. More recently, a headset style of BCI has become available through companies such as Emotiv that has a smaller profile and a more stylized appearance.

SUMMARY

According to one aspect of the present disclosure, a method of helping a particular user use a user interface (UI) is implemented by a computing device. The computing device obtains electroencephalography (EEG) data that indicates brain activity of a particular user during a period in which that user views the UI and/or interprets help information that describes how to use the UI. The EEG data may be obtained from a brain-computer interface (BCI), for example. Based on the EEG data, the computing device selects, from among multiple predefined cognitive states, the one or more cognitive states that characterize the particular user during the period. The computing device assists the particular user to use the UI by customizing the help information for the particular user based on the one or more selected cognitive states.

In some embodiments, the method is further characterized by the computing device selecting, based on the EEG data and from among multiple predefined emotional states, the one or more emotional states that characterize the particular user during the period. In such embodiments, the customizing of the help information for the particular user is further based on the one or more selected emotional states.

In some embodiments, the EEG data includes Event Related Potentials (ERPs) corresponding to individual elements of the UI that the user views and/or corresponding to specific words of the help information the user interprets. In such embodiments, selecting the one or more cognitive states includes comparing the ERPs to one or more ERP thresholds, and determining, from rules that define the cognitive states as a function of said comparing, which of the predefined cognitive states are indicated by the determined ERPs.

In some embodiments, the EEG data includes neural oscillations of the particular user during the period. In such embodiments, selecting the one or more cognitive states includes determining a neural oscillation type based on a frequency of the neural oscillations, comparing an amplitude of the neural oscillations to a neural oscillation threshold for the neural oscillation type, and determining, based on the comparing of the amplitude to the threshold, which of the predefined cognitive states are indicated by the frequency and the amplitude of the neural oscillations.

Gaze tracking data may be used to determine one or more individual elements of the UI to which the one or more predefined cognitive states correspond, and/or to determine one or more individual words of help information to which the one or more predefined cognitive states correspond.

The customizing of help information may include any combination of the following, for example: customizing an organization of help information; adding or removing a definition of a word in a section of help information; increasing or decreasing a level of detail in a section of help information; increasing or decreasing a level of complexity of the language used in a section of help information; adding or removing references to a previous version of the UI in a section of help information; adding or removing a shortcut to help information; and adding a brief snippet of help information, such as a tooltip, to the UI.

In some embodiments, the UI is a graphical user interface of a software program that is accessed using the computing device, and the help information provides instruction on how to use the software program. In some embodiments, the UI is a UI of a machine, and the help information provides information on how to use the machine.

According to one aspect of the present disclosure, a computing device for helping a particular user use a UI is disclosed. The computing device is configured to obtain EEG data that indicates brain activity of a particular user during a period in which that user views a UI and/or interprets help information that describes how to use the UI. The computing device is further configured to, based on the EEG data and from among multiple predefined cognitive states, select the one or more cognitive states that characterize the particular user during the period. The computing device is further configured to assist the particular user to use the UI by customizing the help information for the particular user based on the one or more selected cognitive states.

DETAILED DESCRIPTION

A user's understanding of the functionality of a piece of software or a device changes from user to user. Despite this, in the prior art help information for software and devices has been the same for all users. Also, help information provided with software has not changed over time to reflect a user's change in understanding of the software. The present disclosure provides a way for the understanding of an individual user to be assessed, and for that information used to create a help information (e.g., in the form of a help page) that is personalized to that user's level of understanding. Help information may include any combination of text based information, audio, and video, for example.

A method, apparatus and computer program product for helping a particular user use a UI based on EEG data are disclosed. EEG data is obtained by measuring electrical potentials that indicate brain activity of a particular user during a period in which that user views a UI and/or interprets help information that describes how to use the UI. Based on the EEG data and from among multiple predefined cognitive states, a selection is made of the one or more cognitive states that characterize the particular user during the period. The particular user is assisted to use the UI by customizing the help information for the particular user based on the one or more selected cognitive states.

In some embodiments, the cognitive states are tied to cognitive processes, such as memory, association, language, attention, pattern recognition, problem solving, etc. Because of this, the cognitive state can be used to determine a particular user's familiarity or understanding of some functionality offered by software being used. The cognitive state can relate to the user viewing a UI and/or interpreting help information (e.g., reading help information, listening to audio help information, or listening or watching video help information). In such embodiments, the cognitive states may characterize a state of one of more of the cognitive processes.

Gaze tracking is a technique whereby the location of a person's gaze (for example which area on a computer screen the user is looking at) is monitored. Various systems are available that perform gaze tracking, the most common being the use of a camera to monitor movement of the eye, which together with an understanding of the local environment (e.g., the distance to a screen that is being looked at, relative position of the camera to the screen, etc.) is used to assess the area, e.g., a portion of the UI or an element of the UI, the user is looking at. Gaze tracking may optionally be used in combination with the EEG data described above, such that the obtained EEG data is correlated to specific UI element(s) and/or individual words of help information to which the cognitive state corresponds. By using gaze tracking, the customization can be based on the specific UI element(s) and/or individual words identified. If gaze tracking data is used, an operating system of the computing device customizing the help information (or an operating system of a secondary computing device performing gaze tracking on behalf of the computing device customizing the help information) needs to know the relative location of the physical objects relative to the camera that tracks the user's gaze.

By analyzing EEG data, a computing device providing help information can estimate a person's understanding of the activity they are undertaking on a device (e.g., modifying settings of a software application, an operating system, or the computing device). The estimation of understanding is made via signals measured using a BCI apparatus capable of measuring electrical potentials which represent electrical activity at one or more locations on the user's scalp. The signals from the EEG apparatus can be used to identify instances of degraded understanding of the activity they are undertaking on a device.

A computing device can, in some embodiments, estimate whether a degradation of understanding relates to: the software application being used (i.e., is the user familiar with the application or software being used); a comparison between functions within the software application program being used (e.g., is the user seemingly unfamiliar with a portion of the functionality of the software application being used, while being seemingly familiar with other aspects of the software); and a comparison to functions provided by other software applications (e.g., is the user familiar with similar functionality in other software applications, while having a degraded familiarity or understanding with the functionality within the current software application).

The user's familiarity or understanding of software functionality may be based on one or more of: whether a UI element is recognized, whether a UI element or help information contains words that are not expected by the user, and whether the user's cognitive load appears higher when attempting to use a piece of functionality in comparison to other pieces of functionality offered by the application software.

In accordance with the user's estimated familiarity or understanding of a function, different types of help may be offered. Examples of how the help can be modified include: the content can be modified (e.g., the complexity of language can be changed, or the number and simplicity of examples can be adjusted); the order of content can be modified (e.g., for users with lower familiarity the help text can provide a general description followed by specific functionality, whereas for users with higher estimated levels of familiarity the help text can invert this order by providing the specific functionality first followed by the general description); additional contextual information can be provided (e.g., if a user is seemingly familiar with a similar piece of functionality in a different software application, but seemingly unfamiliar with the current application, then additional contextual information can be provided as to the significance of the functionality in the current application); and if the user appears to have a more distant recollection with regard to a piece of functionality then the help can be modified to describe how the user previously utilized that functionality.

Thus, according to one aspect of the present disclosure, a particular user's brain activity is measured using an EEG apparatus (e.g., a BCI) while the particular user operates a device via its UI. The UI may be a graphical user interface (GUI) delivered via a screen, or physical in the form of objects (e.g., buttons, dials, etc.). The user's gaze may be simultaneously tracked such that the UI elements being viewed at a specific time are known, and such that the EEG measurements can be associated with individual UI elements. The EEG measurements are then used to estimate the user's familiarity and/or understanding of the functionality associated with the UI element. Based on this estimation of familiarity and/or understanding, any help that is accessed by the particular user is tailored in such a way to have a greater likelihood of being appropriate to the particular user's needs.

Figure 4:
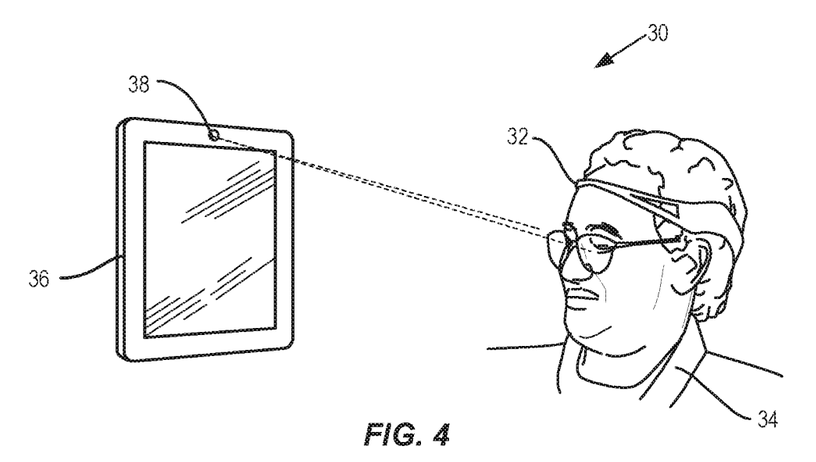
FIG. 4 illustrates an example system for using EEG data to customize help information.

FIG. 4 illustrates an example system 30 for using EEG data to customize help information in which the UI is a graphical user interface (GUI) of a software program that is accessed using computing device 36, and the help information provides instruction on how to use the software program. The system 30 includes a brain computer interface (BCI) 32 operative to record EEG data from a user 34, and includes the computing device 36 which is operative to provide help information to the user 34 (e.g., via its electronic display and/or via speakers). A camera 38 may optionally be included to perform gaze tracking of the user 34 for correlating the EEG data with specific items viewed by the user 34 (see dotted lines indicating gaze tracking). Although the BCI is shown as a headset 32, it is understood that other BCIs may be used (e.g., a scalp cover that includes a plurality of electrodes). Also, although the computing device 36 is shown as a tablet, it is understood that other computing devices could be used, such as laptop computers, desktop computers, smartphones, etc.

Figure 5:
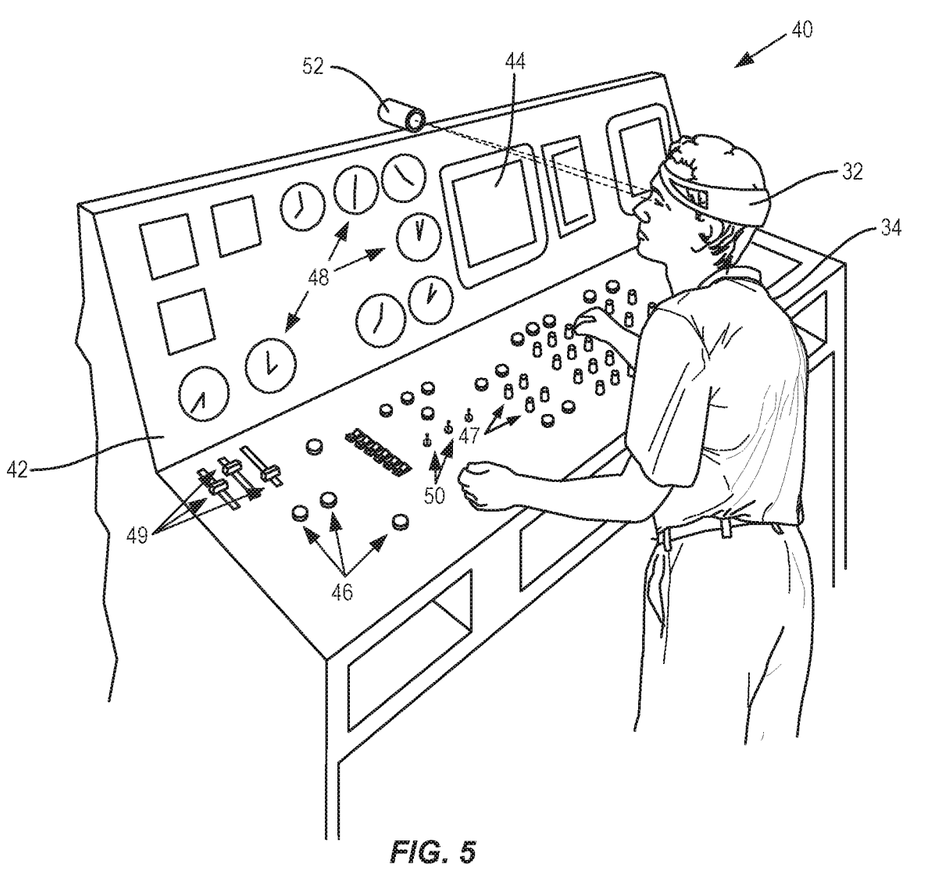
FIG. 5 illustrates another example system for using EEG data to customize help information.

FIG. 5 illustrates an example system 40 for using EEG data to customize help information in which the UI is a UI of a machine 42, and the help information provides information on how to use the machine 42. The system 40 includes the machine 42, a BCI 32 operative to record EEG data from a user 34, and also includes a computing device 44 associated with the machine 42. The computing device 44 is configured to provide help information for the machine 42 (e.g., via its electronic display and/or via speakers). The machine includes a number of controls, including a plurality of buttons 46, knobs 47, dials 48, sliders 49, and switches 50, and may optionally also include a camera 52 to perform gaze tracking of the user 34 for correlating the EEG data with specific items viewed by the user 34 (see dotted lines indicating gaze tracking). In FIG. 5, the UI elements at issue are physical objects, such as physical buttons on a device. It will be appreciated that an alternative environment to the industrial machinery of FIG. 5 could be the interior physical controls of a car.

Figure 6:
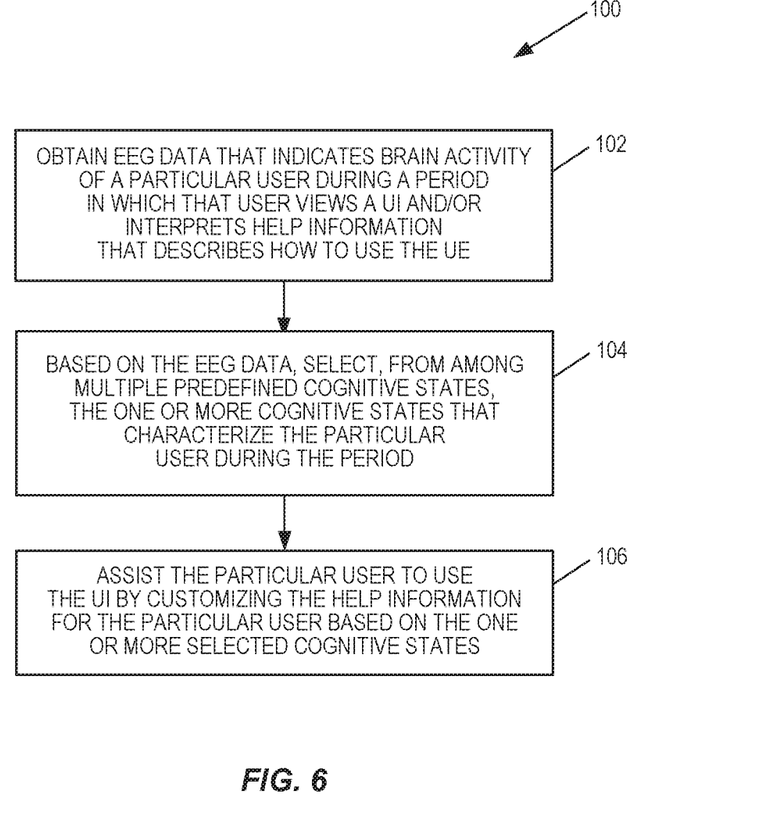
FIG. 6 schematically illustrates an example method of helping a particular user use a user interface (UI).

FIG. 6 illustrates an example method 100 of helping a particular user use a UI. EEG data is obtained (block 102) that indicates brain activity of a particular user during a period in which that user views the UI and/or interprets help information that describes how to use the UI. Based on the EEG data a selection is made (block 104) from among multiple predefined cognitive states of the one or more cognitive states that characterize the particular user during the period. The particular user is assisted (block 106) to use the UI by customizing the help information for the particular user based on the one or more selected cognitive states.

The customization of help information may also be based on emotional states, such as frustration, anger, happiness, excitement, etc., which may or may not be tied to cognitive processes. Thus, in one or more embodiments the method 100 also includes selecting, based on the EEG data and from among multiple predefined emotional states, the one or more emotional states that characterize the particular user during the period. In such embodiments, the customization of block 106 for the particular user is further based on the one or more selected emotional states.

Some example cognitive states may include a default/normal state, an aware state, an unaware state, semantic understanding, a lack of semantic understanding, high cognitive load with understanding, high cognitive load with a lack of understanding, attentive, low attention, and active.

Some example customizations that can be performed for help information may include one or more of the following: creating a customized organization of help information that differs from a default organization of the help information; adding or removing a definition of a word in a section of help information; increasing or decreasing a level of detail in a section of help information; increasing or decreasing a level of complexity of the language in a section of help information; adding or removing references to a previous version of the UI in a section of help information; and adding or removing a shortcut to help information.

Of course these are only example customizations, and it is understood that other customizations could be performed.

In some embodiments, the EEG data obtained in block 102 includes ERPs corresponding to individual elements of the UI that the user views and/or corresponding to specific words of the help information the user interprets. In such embodiments, the selecting of the one or more cognitive states (block 104) includes comparing the ERPs to one or more ERP thresholds, and determining, from rules that define the cognitive states as a function of the comparing, which of the predefined cognitive states are indicated by the determined ERPs. For example, the ERP P300 being greater than a threshold x could indicate a first cognitive state, and being less than the threshold x could indicate a different second cognitive state. Some example rules are shown in Table 1, which is discussed in more detail below. Prior to being compared to the one or more ERP thresholds, the ERP data (e.g., signals from which the ERPs are calculated) may be processed in some way (e.g., any combination of filtering, normalizing, value averaging, etc.). Thus, when used herein, "ERP data" may refer to a processed ERP signal, an ERP signal that omits such processing, or a combination thereof.

Determining the ERPs may be based on specific items viewed by the particular user. In some embodiments, obtaining EEG data that indicates brain activity of the particular user (block 102) includes: obtaining EEG measurements from a BCI configured to measure EEG data from the particular user's brain during the period, and determining the ERPs based on the EEG measurements and based on times at which the user views the individual elements of the UI and/or times at which the user interprets the help information that describes how to use the UI.

The times at which the user views the individual elements of the UI and/or interprets help information can be determined using gaze tracking data, for example.

Neural oscillations (NOs) may be used as the basis for the help information customizations, either alone, or in combination with ERPs. Thus, in some embodiments, the EEG data includes neural oscillations of the particular user during the period. In such embodiments, selecting the one or more cognitive states (block 104) includes the following: determining a neural oscillation type based on a frequency of the neural oscillations; comparing an amplitude of the neural oscillations to a neural oscillation threshold for the neural oscillation type; and determining, based on the comparing of the amplitude to the threshold, which of the predefined cognitive states are indicated by the frequency and the amplitude of the neural oscillations.

In some such embodiments, obtaining EEG data that indicates brain activity of the particular user (block 102) includes obtaining EEG measurements from a BCI configured to measure EEG data from the user's brain during the period, and determining, from the EEG measurements, the frequency and amplitude of neural oscillations of the user during the period. Thus, the EEG data may include a set of frequencies and amplitudes of neural oscillations, or may include the wave forms representing the neural oscillations such that the computing device performing method 100 needs to determine the frequencies and amplitudes itself from the waveforms.

In embodiments in which gaze tracking data is used, the customization of help information may be based on specific UI elements viewed and/or specific sections of help information viewed. The section of help information to which EEG data is correlated could vary in size (e.g., several paragraphs on a topic, or several words from a single sentence). For example, a customization could be performed based on a user being frustrated while reading several paragraphs of help information. As another example, a customization could be performed based on a user having a semantic misunderstanding within a phrase or sentence that is much shorter.

In some embodiments in which gaze tracking data is used, obtaining the EEG data (block 106) includes determining the EEG data based on gaze tracking data that indicates which individual elements of the UI the user views during the period. In some of these embodiments, the method 100 also includes determining, based on the EEG data, one or more individual elements of the UI to which the one or more predefined cognitive states correspond. The customizing of block 106 for the particular user is then further based on the one or more individual elements of the UI to which the one or more predefined cognitive states correspond.

In some embodiments where gaze tracking data is used, obtaining the EEG data (block 106) includes determining the EEG data based on gaze tracking data that indicates which help information the user views during the period. In such embodiments, the method 100 also includes determining, based on the EEG data, one or more individual words of the help information to which the one or more predefined cognitive states correspond. The customizing of block 106 for the particular user is then further based on the one or more individual words of the help information to which the one or more predefined cognitive states correspond.

Table 1, shown below, lists example cognitive states, descriptions of those cognitive states, and conditions that can cause the cognitive states. The conditions can refer to the amplitude of various ERPs, or the amplitude of various neural oscillations, for example. Table 2 presents similar information, but for emotional states. Table 3, meanwhile, lists example customizations that can be performed for a given cognitive or emotional state.

TABLE 1

Example Cognitive State Lookup Table

| Condition | Event | Cognitive State | Description |
|---|---|---|---|
| Baseline ERP and neural oscillations | | Default/ normal state | User is not confused and understands UI items they are viewing |
| $P300 < x$ | Viewing image | Aware/ Understanding | Use is aware of a visual stimuli |
| $P300 > x$ | Viewing image | Not aware/ Misunderstanding | Use is not aware of and/ or misunderstands a visual stimuli |
| $N400 > y$ | Viewing word in sequence of text | Semantic understanding | Word makes sense in context |
| $N400 < y$ | Viewing word in sequence of text | lack of semantic understanding | Word does not make sense in context |
| $P300 < x$ and $N400 < y$ | Viewing image and text | Aware + Lack of semantic understanding | Use is aware of a visual stimuli but does not understand text |
| $P300 > x$ and $N200 < y$ | Viewing image and text | Not aware + lack of semantic understanding | Use is not aware of a visual stimuli and does not understand text |
| $P300 > x$, $n400 < y$, high amplitude theta waves, high amplitude beta waves | Viewing image and/or text | High cognitive load (lack of understanding) | User has to think a lot about what they are viewing, does not recognize items on the screen, and is confused by the text used. This could indicate confusion. |
| $P300 > x$, $n400 > y$, high amplitude theta waves, high amplitude beta waves | Viewing image and/or text | High cognitive load (with understanding) | User has to think a lot about what they are viewing. This could indicate that the user is undertaking a complex task. |
| High amplitude alpha waves | n/a | Low attention | Associated with being relaxed, drowsiness and sleep |
| Low amplitude alpha waves | n/a | Attentive | User is attentive to external stimuli |
| High amplitude beta waves | n/a | Active | Active, busy, anxious thinking, |

TABLE 1-continued

Example Cognitive State Lookup Table

| Condition | Event | Cognitive State | Description |
|---|---|---|---|
| | | | active concentration. Exerting mental effort, retrieving memories. |

In some embodiments, if the "default/normal state" is detected, then no customization is performed on help information presented to the particular user. Of course, this is only an example, and it is understood that in some embodiments customization may always be performed.

The thresholds shown in Table 1 may be user-specific thresholds that are determined based on baseline EEG data for the particular user and/or baseline EEG data for one or more other users. For example, when initiating a software program, a user may be asked about a feature that they understand well, and an inference could be made that the user has a good understanding of that feature. As another example, an automatic detection may be made of a UI element that is frequently used by the user, and an inference could be made that the frequently used UI element represents a feature that is well-understood by the user. This could be performed automatically without "asking" the user as in the previous example, such that the user may be unaware of what feature is being used to determine their baseline EEG data. By having baseline EEG data, a more accurate determination can be made of the delineation between various cognitive states. EEG data from other users may also be used. For example, if some features are very commonly used by many users (e.g., a 'Save' button), an inference may be made that the commonly used feature is well-understood by most users, and based on that a prediction may be made that the particular user will also understand that given feature.

Help information can also be customized based on the emotional state of the particular user. For example, if a given user is frustrated, angry, happy, etc., then help information provided to the particular user may be customized accordingly. Table 2, shown below, lists an example emotional state, a description of the emotional state, and a condition that can cause the emotional state. It is understood that the use of emotional states is optional, and that in some embodiments only cognitive states may be used for customizing help information. Also, it is understood that other emotional states not shown below could be used as the basis for customizing help information.

TABLE 2

Example Emotional State Lookup Table

| Condition | Event | Cognitive State | Description |
|---|---|---|---|
| High amplitude theta waves | n/a | Frustration | Theta waves will occur for brief periods during an emotional response to frustrating events or situations |

In one example, an emotional state of a user is determined based on an asymmetry of frontal lobe EEG measurements (e.g., if the right side of the front of the brain has a high EEG signal and the left side low, or vice versa).

Table 3, shown below, lists example cognitive and emotional states, and example descriptions of the customizations that can be applied to help information based on those states.

TABLE 3

Example Customizations

| Cognitive/ Emotional State | Customization Action |
|---|---|
| Normal/ default state | No customization of help performed. |
| High cognitive load (lack of understanding) | Organize help so that information is presented in a simple way, with a clarification step after each segment of new information (ii) If the user has spent time in this cognitive state (and therefore has spent effort trying to understand), organize help such that it has a list whereby the user is asked what aspects they do or do not understand and then provide additional details for the sections that are not understood (either user could state what they don't understand or their User State could be determined using EEG). |
| Not aware (looking at an icon, first use of an application) | Because user does not recognize image they are looking at, use a 'quick tip' to provide a written description of the icon, as it may just be that the user does not associate the icon with some known functionality. |
| Aware + High cognitive load (understanding) | User is thinking hard, and is understanding what he/she is doing. Organize help so that 'parameter' style information is presented first (e.g., a table of symbols/functions with their meanings/ parameters is presented first on the assumption that the user generally knows/understands the function but is searching for a small detail). |
| Aware (application icon) + Not aware (functionality icon) | Present the help in a way that explains the new functionality, but consider the reader to be someone who is has an understanding of other aspects of the application in question (i.e., treat as a new function the user has not seen before, but in an application that the user is familiar with). |
| Lack of semantic understanding | Either explain what words mean or provide an alternate set of words. |
| Awareness + Lack of semantic understanding | For example the user may recognize the icon but is confused by the written explanation. This may be due to some changes between versions in the application, in which case organize help so it refers back to the previous version. Alternatively, the functionality may have some specific nuances that could be explained. |
| Low attention | Present help in a way more likely to grab attention, for example an animated character could interact with the user. |
| Attentive | The user is interested in the topic. Provide 'find out more' sections at the end of the help information. |
| Frustration | Organize help such that the user can experience a successful interaction to reduce frustration. For example the user could interact with the device to perform a function, but do so in a way where the interaction is broken down into sections, allowing the user to experience several small successes as they complete each section. |

In some embodiments the customizing of help information (block 106) for the particular user includes customizing an organization of help information if the cognitive state indicates high cognitive load or awareness of an element of the UI, or if the emotional state is frustration.

In some embodiments the customizing of help information (block 106) for the particular user includes adding or removing a definition of a word in a section of help information if the selected one or more cognitive states indicate a lack of a semantic understanding.

In some embodiments if the selected one or more cognitive states indicate a high cognitive load, the customizing of help information (block 106) for the particular user includes increasing or decreasing a level of detail in a section of help information and/or increasing or decreasing a level of complexity of the language used in a section of help information.

In some embodiments, the selected one or more cognitive states indicate a lack of semantic understanding and/or awareness of an element of the UI, and the customizing of help information (block 106) for the particular user includes adding or removing references to a previous version of the UI in a section of help information. This particular cognitive state could occur if a user recognizes an icon but is confused by the written explanation for the icon, possibly because of some changes between versions in the application. The adding or removing references to a previous version of the UI could include providing the old name of the UI element and/or providing an explanation of how the UI element worked in the previous release compared to how it works in the current release being used by the particular user.

In some embodiments, the selected one or more cognitive states indicate a lack of awareness and/or a lack of semantic understanding, and the customizing of help information (block 106) for the particular user includes adding or removing a shortcut to the help information and/or adding a brief snippet of help information to the UI (e.g., a so-called "quick tip" or a "tooltip" which is displayed when the user hovers a pointer of a graphical UI, such as a mouse pointer, over a UI element).

Figure 7:
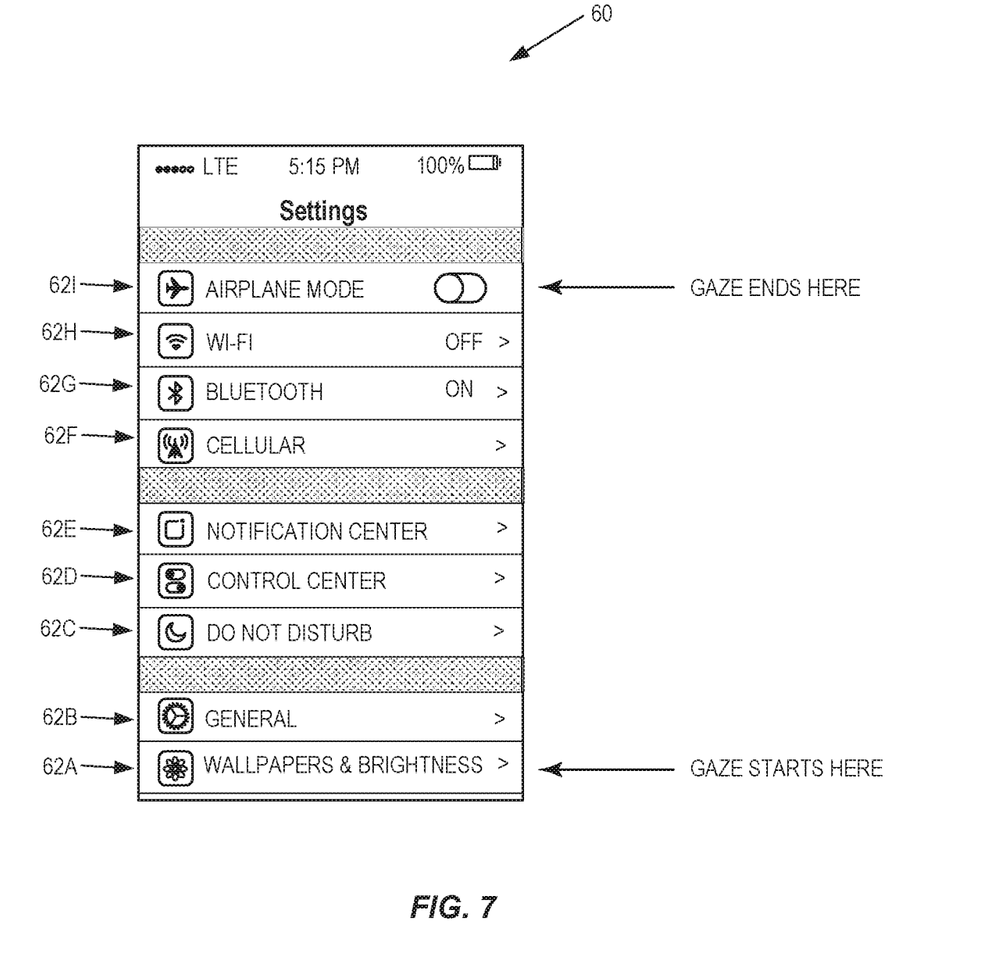
FIG. 7 illustrates an example user interface.

Referring now to FIG. 7, an example user interface 60 is shown which includes a plurality of UI elements that include settings 62A-62I for a smartphone or tablet computing device. Assume that the user is looking at the settings starting from the bottom up, such that the setting 62A for "Wallpapers & Brightness" is viewed first and the setting 62I for "Airplane Mode" is viewed last. Assume also that the user understands each of the settings 62A-62H but is confused by the setting 62I for "Airplane Mode." An ERP signature of the particular user will reflect that they are familiar with settings 62A-H and are not familiar with setting 62I. For example, the user's P300 response may be below a threshold x for each of settings 62A-I but may be above that threshold for setting 62I, indicating that the user has a lack of understanding of the setting 62I.

The computing device implementing method 100 can respond in several ways. In some examples, the help may be automatically provided. In one example, the computing device could automatically provide a "quick tip" for that feature, such that a brief snippet of text is provided to explain the "Airplane Mode" and to serve as a link to more information about the airplane mode. This could be done automatically based on the EEG data without the user actually requesting help. In another example, the computing device could present an icon or other indicator next to "Airplane Mode" to indicate that help is available for "Airplane Mode" (e.g., a light bulb or some other icon appearing next to the setting 62I for "Airplane Mode"). In another example, no automated help is presented, but when the particular user requests help for the interface 60, the help presented for "Airplane Mode" is listed first, or is explained in greater detail.

In the prior art, the help associated with a piece of software or device is typically either ON (such that tips are given, e.g., the first time a piece of functionality is used), or is provided to the user on request (e.g., when the user clicks on a "Help" button). The present disclosure provides techniques for automatically providing help based on EEG data when a particular user has a cognitive state and/or emotional stated that is commensurate with the need for help. This enables help information to be personalized for an individual user and/or to be more appropriate to the user's understanding of the software.

Referring again to FIG. 7, as another example, assume that EEG data for the particular user indicates that the user is generally frustrated (not necessarily at a particular UI element, but just in general). As described in Table 2 above, this may be detectable if the particular user has neural oscillations that are theta waves with high amplitude (i.e., amplitude above a predefined threshold). Help for the particular user could be customized such that the user can experience a successful interaction to reduce frustration (see last row of Table 3 above).

In some embodiments, the method 100 includes three separate processes: A) cognitive and/or emotional state determination: determining which specific UI element or UI element sequence to which the user's cognitive and/or emotional state corresponds; B) help request: receiving a help request whereby the user requests help; and C) PHP creation: creation of a customized, personalized help page (PHP) that includes help information customized for the particular user based on activity being undertaken by the user and their cognitive and/or emotional state.

Each of these processes is discussed in greater detail below.

Cognitive and/or Emotional State Determination

In some embodiments, the determination of the user's cognitive and/or emotional state includes the following: i) tracking the particular user's gaze with respect to the location of a camera; ii) an operating system (OS) of the computer, or an application software being executed on the computer, implementing method 100 associating the location of the user's gaze to a specific location on the screen, and thus to a UI areas, and thus to specific UI elements; iii) the operating system (OS), or the application software, recording the time the gaze enters and exits the UI area; and iv) measuring of electrical activity on the particular user's scalp using a BCI.

A processing unit within the computing device implementing method 100 separates a number of specific ERPs and records each of these, together with the time of its occurrence. The computing device takes the EEG data signals and determines the user's cognitive and/or emotional state. Here, the initiation of an event is defined as the time the user's gaze enters a UI area. For example, the cognitive and/or emotional state may be determined by performing the following: i) determining that an ERP is above or below a certain threshold stored in a lookup table (e.g., Table 1 or 2 above); ii) normalizing the ERP for a first UI element with respect to a second UI element, which is known to be well understood by the user, and determining the normalized value is above a certain value; iii) determining whether a sequence of ERPs as the user moves between UI areas matches a pattern described in an ERP lookup table (e.g., Tables 1-2 above).

Similar steps could be performed to determine what section of help information was viewed by a user, and to determine ERPs accordingly. As discussed above, a section of help information can vary in size (e.g., several paragraphs on a topic, or several words from a single sentence).

Where it is beneficial to either normalize the ERP, or use a comparative ERP measurement versus a known signal (e.g., one associated with functionality that the user is familiar with and understands well), then certain well understood and commonly used functions such as 'Save' or those that associated with icons that are consistent across a variety of software, are designated as reference ERP signals (e.g., for determining a "baseline" for a given user). In this regard a cognitive and/or emotional state can be associated with a specific UI element or piece of help information (or a sequence of UI elements or pieces of help information, respectively).

Help Request

In this process, the particular user requests help. Examples of how this might be done include: by interacting with the OS or the application software (e.g., pressing a button or link or giving a specific voice command), by using a setting such that help is automatically displayed once a specified cognitive and/or emotional state (or sequence of states) are detected, and/or by using a setting such that help is automatically provided once an ERP, or normalized ERP, reaches a specified threshold.

As used herein, "normalization" can refer to any of a number of standard mathematical forms (e.g., standard deviation, standard score, mean, etc.). For example, normalization could refer to adjusting two values measured on different scales to a common scale. Thus, if a measurement "A" on a scale of 0 to 20 was 4, and a measurement "B" on a scale of 0 to 50 was 5, then normalizing the two sets to a scale of 0 to 1 would mean A(normalized)=0.2 and B(normalized)=0.1.

PHP Creation and Display

Once help has been requested and the cognitive and/or emotional states for a given set of UI elements and/or sections of help information are known, customized help information may be generated. The customized help information could be presented in the form of a personalized help page (PHP), for example. Alternatively, the customized help information could be provided in other ways (e.g., on other forms than a page, such as audio playback while the user continues viewing the UI). An example of how customized help information may be created can include the following.

Sections of help information may be organized as "help segments," each being (i) categorized by function, and where appropriate (ii) associated with a given UI element and (iii) ranked or tagged using a set of Information Classifiers (ICs). Some examples of ICs together with ranking and tagging schemes may include: i) Description Complexity—ranked from 1 being low complexity to 3 being high complexity; ii) Context Level—ranked from 1 being OS level, level 2 being application, level 3 being functional, etc. to a being control element (e.g., button or slider); iii) Pre-requisite knowledge—being the ID tag of other information sets in the Help Database; iv) Specific Tags—the tags provide information about a given help segment. For example: a) High Density Information (HDI)—a succinct set of text or graphics containing a high amount of information (e.g., a table containing a list of parameters and their usage); b) Additional Content (AC)—being additional material to be displayed if a user's cognitive state is at a certain level, e.g., if the user shows either very high or low understanding.

When help is requested, a set of help segments is determined. This may be achieved by performing the following: if the user requests help on a specific function, then this is directly related to specific help segments; if the requirement for help is triggered by a particular cognitive state for a given UI element (or sequence of UI elements) then help is given for functionality associated with that UI element (or sequence of UI elements); if the user requests help but does not specify a function, then the recent viewing history of UI elements can be assessed and a set of help segments inferred; and for each case the result is the OS has a list of relevant help segments, that also include IC information.

In one example, if EEG data for a particular user indicates that the user does not understand a feature (e.g., "Airplane Mode" above), and help is requested without specifying a specific topic, then the computing device implementing method 100 may provide a suggestion (e.g., "Do you want help on 'Airplane Mode'?").

A Customization Algorithm then compares the cognitive and/or emotional states for given UI elements and compares these, and sequences of these to threshold values in a lookup table, which then returns: the ICs together with the tags and ranking that should be used to select help segments from a help database; and the order the help segments that should be displayed.

The help segments and order of display derived from the preceding step are used to compile customized help information (e.g., a PHP) and the customized help information is then presented to the user.

Some of the embodiments discussed above have discussed customizing help information based on a single user obtaining help for a single software program. The estimation of familiarity and understanding is made via EEG data of the user alone within the context of a single software application. However, a number of alternatives are possible.

For example, EEG data may be compared among multiple users. This could include the ability to compare either the particular user's EEG measurements, or the estimation of familiarity or understanding inferred from those EEG measurements, with other user's information. With such a system the estimation of a user's familiarity or understanding could potentially be made with greater accuracy.

In some embodiments, the modification of text performed when customizing help information could be made in such a way that the particular user is more likely to find it beneficial (e.g., once modifications are known that helped or did not help other users exhibiting similar patterns of familiarity or understanding, it is more likely that a suitable configuration could be found for the user in question). In such systems, the method 100 could include determining that a given customization of help information that describes how to use the UI was helpful to a different user that exhibited one of the one or more selected cognitive states when that different user viewed the UI and/or interpreted help information that describes how to use the UI. In such an embodiment, the customizing of block 106 could be further based on the given customization. Whether or not a customization was "helpful" could be determined, e.g., by asking a given user to provide a rating to the help information recently provided to them.

The customization of help information may include EEG measurements made while the particular user is using other software programs, for example if two icons are each presented in a different software application, and are similar in appearance (as ascertained by an image comparison algorithm), yet the user seemingly has a low understanding of one and a high understanding of the other then it is more likely it is the contextual use of that functionality that is causing the lack of understanding. In such embodiments, the method 100 may include: determining one or more additional cognitive states that characterize a state of the particular user when the user views a different UI and/or the help information that describes how to use the different UI; and comparing the one or more selected cognitive states to the one or more additional cognitive states. In such embodiments, the customizing of block 106 could be further based on the one or more additional cognitive states of the different UI.

Additional physiological measurements that can be correlated to a user's understanding may also be taken in order to reduce the effects of signal noise, and more accurately identify the cognitive state that characterizes the particular user. This could include, for example, body temperature, blood pressure, heart rate, etc. Such additional physiological measurements could thereby improve the personalization of help information by more accurately categorizing the state of the user at a given time.

As discussed above, in some embodiments help information may be organized as "help segments," each being (i) categorized by function, and where appropriate (ii) associated with a given UI element and (iii) ranked or tagged using a set of Information Classifiers (ICs). Help segments may include segments of text, images, tables etc. which when combined form a coherent help page. Help segments may also include audio and/or video files that can be played back for a user as help information. The audio and/or video files may be embedded on a personalized help page (PHP), for example.

As discussed above, gaze tracking may be used to correlate EEG data with a particular UI element and/or with a particular section of help being viewed. A UI element can include a graphic or object on a screen that conveys some meaning and/or offer the option to carry out an action or organize the displayed content. Examples of UI elements include icons, control objects (e.g., buttons volume sliders, On/Off sliders), and text segments (e.g., "Airplane Mode" in FIG. 7). In some examples, UI elements may be overlapping (e.g., a first UI element which is a button may be fully contained within a second UI element which is a panel). In other embodiments, UI elements may be physical devices on a machine (e.g., buttons 46, knobs 47, dials 48, sliders 49, and switches 50 on machine 42 in FIG. 5). Thus, the UI elements may be GUI elements (FIG. 4), but may also be non-GUI, i.e., physical, elements (FIG. 5).

When correlating gaze tracking and EEG data, the notion of a "UI element area" may be used, which refers to a geometric area associated with a given UI element or section of displayed help information. UI element areas may be in the form of rectangles, circles, or any other such shape that can be geometrically described. UI element areas may be used by the OS performing the correlating of gaze tracking data with EEG data.

In some examples, the customization of help information may be based on a sequence of viewed UI elements. These elements could be viewed sequentially by the user (e.g., as discussed in connection with FIG. 7), or could be viewed according to some sort of pattern (e.g., the user may look at a button, then a section of text, then at the button again).

Figure 8:
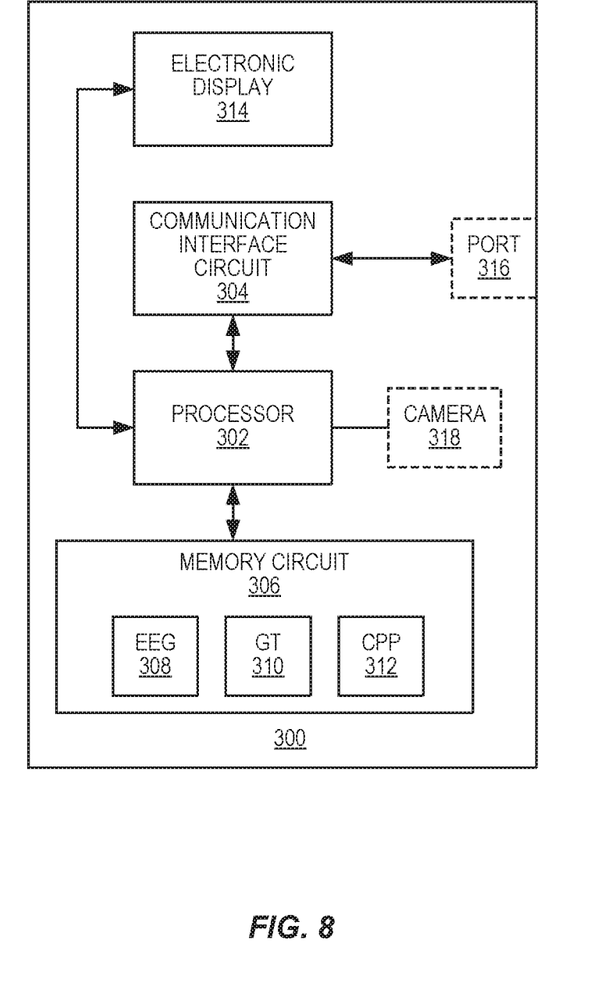
FIG. 8 schematically illustrates an example computing device configured to customize help information based on EEG data.

FIG. 8 illustrates an example computing device 300 configured for helping a particular user use a UI by customizing help information based on EEG data. The computing device includes a processor 302, communication interface circuit 304, and memory circuit 306. The processor 302 includes one or more processor circuits, (e.g., one or more microprocessors, microcontrollers, digital signal processors, application specific integrated circuit (ASIC), or the like) configured with appropriate software and/or firmware to carry out one or more of the techniques discussed above. The communication interface circuit 304 obtains EEG data from a BCI (not shown) that measures the EEG data from a particular user through either a wireless interface, or a wired interface. If wireless communication is used, the communication interface circuit 304 may be configured according to one or more known wireless communication standards (e.g., 3GPP or 802.11 standards). If wired communication is used, the communication interface circuit 304 may obtain EEG data through an optional input port 316. The memory circuit 306 may include one or several types of memory such as read-only memory (ROM), random-access memory, cache memory, flash memory devices, optical storage devices, etc.

The computing device 300 is configured to help a particular user use a user interface (UI). In particular, the processor 302 is configured to obtain EEG data that indicates brain activity of a particular user during a period in which that user views a UI and/or interprets help information that describes how to use the UI. The processor 302 is further configured to select, based on the EEG data and from among multiple predefined cognitive states, the one or more cognitive states that characterize the particular user during the period. The processor 302 is further configured to assist the particular user to use the UI by being configured to customize the help information for the particular user based on the one or more selected cognitive states.

The customized help information is displayed on an electronic display 314 that is either in communication with the computing device 300 (e.g., an external display) or is part of the computing device 300 (e.g., an embedded display). In some embodiments, the UI for which help information is provided is a graphical user interface (GUI) presented on the electronic display 314. In other embodiments, the UI is a UI for a device (e.g., buttons, knobs, dials, switches, sliders, etc. as shown in FIG. 5) and the help information for that UI is provided on the electronic display 314. The computing device 300 runs an operating system such that, in some embodiments, information is presented to the particular user in a graphical manner.

EEG data 308 is received through the communication interface circuit 304 and may be stored in the memory circuit 306. In some embodiments, the computing device 300 includes a camera 318 operative to record images of the eyes of the particular user during a viewing period to obtain gaze tracking data 310 which may be stored in memory circuit 306. The gaze tracking data 310 may be correlated with the EEG data to determine with specific UI elements and/or specific sections of help information to which the EEG data corresponds. In some embodiments, the gaze tracking data 310 is either received from another computing device, or is omitted entirely. Customizable help information for the UI in question is stored either in memory circuit 306 or another memory device (e.g., as help segments in a help database).

Although a tablet computing device 36 is shown in FIG. 4, it is understood that the computing device 300 of FIG. 8 may include any number of computing devices, such as smartphones, tables, car dashboards, home automation interfaces, laptop computers, desktop computers, etc.

In some embodiments, the computing device 300 includes a computer program product (CPP) 312 stored in a non-transitory computer-readable medium (e.g., memory circuit 306) for helping a particular user use a UI. The computer program product includes software instructions which, when run by processor 302 of the computing device 300, configures the computing device 300 to: i) obtain electroencephalography (EEG) data that indicates brain activity of a particular user during a period in which that user views a user interface (UI) and/or interprets help information that describes how to use the UI; ii) based on the EEG data, select, from among multiple predefined cognitive states, the one or more cognitive states that characterize the particular user during the period; and iii) assist the particular user to use the UI by customizing the help information for the particular user based on the one or more selected cognitive states.

In embodiments where gaze tracking is used, there is an operating system (OS) running on the computing device 300, and the OS can determine size and location of various UI elements and/or sections of help information, and can determine the start and end time a UI element (or section of help information) is displayed on the electronic display 314. In such embodiments, if a camera 318 is included, and the OS knows the location of the camera with respect to the electronic display 314 and a relative angle of the electronic display 314 and camera 318 with respect to the particular user, then the computing device 300 can record gaze tracking data for a given user. In other embodiments, gaze tracking data may be received from another computing device. In the memory circuit 306, a lookup table (e.g., Tables 1-2) may be stored that associates ERP signals derived from a BCI with cognitive states and/or emotional states.

The various embodiments discussed above provide improvements over the prior art. Techniques are provided to customizing help information for a UI in a way that reflects the understanding of individual users. Thus, as a user's understanding of the UI changes over time, different customizations can be performed. Also, in some embodiments, help information can be customized based on an emotional state of the user, which can make interpreting that help information a more positive experience for the user.

The present disclosure may, of course, be carried out in other ways than those specifically set forth herein without departing from essential characteristics of the present disclosure. The present embodiments are to be considered in all respects as illustrative and not restrictive, and all changes coming within the meaning and equivalency range of the appended claims are intended to be embraced therein.

The invention claimed is:

1. A method of helping a user use a user interface (UI), the method comprising:
    obtaining electroencephalography (EEG) data that indicates brain activity of the user during a period of time in which the UI is viewable to the user and/or help information that describes how to use the UI is output to the user;
    based on the EEG data, estimating the user's understanding of functionality associated with the UI; and
    based on the estimated user's understanding of the functionality associated with the UI, assisting the user to use the UI.

2. The method of claim 1, wherein estimating the user's understanding of functionality associated with the UI comprises estimating the user's familiarity or understanding of some functionality offered by a software being used.

3. The method of claim 1, wherein estimating the user's understanding of functionality associated with the UI comprises estimating the user's familiarity or understanding of an activity which the user is undertaking on a computing device.

4. The method of claim 1, wherein estimating the user's understanding of functionality associated with the UI is based on one or more of:
    whether a UI element is recognized,
    whether a UI element or help information contains words that are not expected by the user, or
    whether the user's cognitive load appears higher when attempting to use a piece of functionality in comparison to other pieces of functionality offered by a software being used.

5. The method of claim 1, further comprising:
    tracking the gaze of the user; and
    based on the tracked gaze of the user, associating the EEG data with one or more elements of the UI.

6. The method of claim 5, wherein
    associating the EEG data with one or more elements of the UI based on the tracked gaze of the user comprises determining, based on the tracked gaze of the user, one or more individual elements of the UI that the user is viewing and associating the EEG data with the one or more individual elements of the UI, and
    assisting the user to use the UI comprises assisting the user to use the UE based on the one or more individual elements of the UI.

7. The method of claim 1, wherein assisting the user to use the UI comprises modifying the content of help information.

8. The method of claim 7, wherein modifying the content of help information comprises one or more of:
    changing a complexity of language,
    adjusting a number and/or simplicity of examples,
    modifying an order of the content,
    providing additional contextual information, or
    modifying the help information to describe how the user previously utilized a similar piece of functionality in a different software application.

9. The method of claim 1, wherein estimating the user's understanding of functionality associated with the UI comprises selecting, from among multiple predefined cognitive states, one or more cognitive states that characterize the user during the period of time.

10. A computing device for helping a user use a user interface (UI), the computing device comprising:
    memory; and
    processing circuitry coupled to the memory, wherein the computing device is configured to:
        obtain electroencephalography (EEG) data that indicates brain activity of the user during a period of time in which the UI is viewable to the user and/or help information that describes how to use the UI is output to the user;
        estimate the user's understanding of functionality associated with the UI based on the EEG data; and
        assist the user to use the UI based on the estimated user's understanding of the functionality associated with the UI.

11. The computing device of claim 10, the memory contains instructions executable by the processing circuitry.

12. The computing device of claim 10, wherein the computing device is configured to estimate the user's understanding of functionality associated with the UI by estimating the user's familiarity or understanding of some functionality offered by a software being used.

13. The computing device of claim 10, wherein the computing device is configured to estimate the user's understanding of functionality associated with the UI by estimating the user's familiarity or understanding of an activity which the user is undertaking on the computing device.

14. The computing device of claim 10, wherein the computing device is configured to estimate the user's understanding of functionality associated with the UI based on one or more of:
    whether a UI element is recognized, whether a UI element or help information contains words that are not expected by the user, or whether the user's cognitive load appears higher when attempting to use a piece of functionality in comparison to other pieces of functionality offered by a software being used.

15. The computing device of claim 10, further being configured to:

track the gaze of the user; and based on the tracked gaze of the user, associate the EEG data with one or more elements of the UI.

16. The computing device of claim 15, wherein the computing device is configured to associate the EEG data with one or more elements of the UI based on the tracked gaze of the user by determining, based on the tracked gaze of the user, one or more individual elements of the UI that the user is viewing and associating the EEG data with the one or more individual elements of the UI, and the computing device is configured to assist the user to use the UI based on the one or more individual elements of the UI.

17. The computing device of claim 10, wherein the computing device is configured to assist the user to use the UI by modifying the content of help information.

18. The computing device of claim 17, wherein the computing device is configured to modify the content of help information by performing one or more of:

changing a complexity of language, adjusting a number and/or simplicity of examples, modifying an order of the content, providing additional contextual information, or modifying the help information to describe how the user previously utilized a similar piece of functionality in a different software application.

19. The computing device of claim 10, wherein the computing device is configured to estimate the user's understanding of functionality associated with the UI by selecting, from among multiple predefined cognitive states, the one or more cognitive states that characterize the user during the period of time.

20. The computing device of claim 10, wherein the EEG data is obtained from a brain-computer interface (BCI) that measures the EEG data from the user.

21. A computer program product comprising a non-transitory computer readable medium storing instructions for configuring a computing device to:

obtain electroencephalography (EEG) data that indicates brain activity of a user during a period of time in which a user interface (UI) is viewable to the user and/or help information that describes how to use the UI is output to the user;

estimate the user's understanding of functionality associated with the UI based on the EEG data; and assist the user to use the UI based on the estimated user's understanding of the functionality associated with the UI.

* * * * *